US006153738A

United States Patent [19]

Jacobsen et al.

[11] Patent Number: 6,153,738

[45] Date of Patent: Nov. 28, 2000

[54] CONTRYPHAN PEPTIDES

[75] Inventors: Richard Jacobsen, Menlo Park, Calif.; Elsie Jimenez, Quezon, Philippines; Lourdes J. Cruz, Salt Lake City, Utah; Baldomero M. Olivera, Salt Lake City, Utah; William R. Gray, Salt Lake City, Utah; Michelle Grilley, Seattle, Wash.; Maren Watkins; David R. Hillyard, both of Salt Lake City, Utah

[73] Assignee: University of Utah Research Foundation, Salt Lake City, Utah

[21] Appl. No.: 09/466,138

[22] Filed: Dec. 21, 1999

Related U.S. Application Data

[62] Division of application No. 09/061,026, Apr. 16, 1998.
[60] Provisional application No. 60/068,737, Dec. 24, 1997.

[51] Int. Cl.[7] ........ C07H 21/04
[52] U.S. Cl. ........ 536/23.1; 536/23.5; 530/857
[58] Field of Search ........ 530/300, 328; 536/23.1, 23.5

[56] References Cited

FOREIGN PATENT DOCUMENTS

| | | |
|---|---|---|
| 9820026 | 5/1998 | WIPO . |
| 9831705 | 7/1998 | WIPO . |

OTHER PUBLICATIONS

Jacobsen, R. et al. (1998). "The contryphans, a D–tryptophan–containing family of Conus peptides: interconversion between conformers." *J. Peptide Res.* 51:173–179.

Jimenez, E.C. et al. (1997). "Bromocontryphan: Post–Translational Bromination of Tryptophan." *Biochemistry* 36:989–994.

Jimenez, E.C. et al. (1996). "Contryphan Is a D–Tryptophan–containing Conus peptide." *J. Biol. Chem.* 271:28002–28005.

*Primary Examiner*—Karen Cochrane Carlson
*Assistant Examiner*—Holly Schnizer
*Attorney, Agent, or Firm*—Rothwell, Figg, Ernst & Manbeck, P.C.

[57] ABSTRACT

The present invention is directed to contryphan peptides having 6–12 amino acids, preferably including one or more D-tryptophan or D-leucine residues. The peptides of the present invention are generically termed "contryphans," although the D-leucine containing contryphans are sometimes referred to as leu-contryphans. More specifically, the present invention is directed to contryphan peptides having the general formula $Xaa_1$-Cys-$Xaa_2$-$Xaa_3$-$Xaa_4$-Pro-$Xaa_5$-Cys (SEQ ID NO:1), wherein $Xaa_1$ is any amino acid or des-$Xaa_1$, $Xaa_2$ is Pro, 4-trans-hydroxyproline or Val, $Xaa_3$ is D-Trp, L-Trp, D-Leu or L-Leu, preferably D-Trp or D-Leu, $Xaa_4$ is any amino acid and $Xaa_5$ is Trp or Tyr. When the peptide contains $Xaa_1$, it is preferably Gly, Glu, or Lys, most preferably Gly. When $Xaa_3$ is D- or L-Trp, $Xaa_2$ is preferably Pro or 4-trans-hydroxyproline. When $Xaa_3$ is D- or L-Leu, $Xaa_2$ is preferably Val. The carboxy terminus may contain a carboxyl or an amide, preferably an amide. The present invention is further directed to the specific contryphan peptides and propeptides as described herein. The present invention is also directed to nucleic acids encoding the contryphan peptides and their propeptides as described herein. The contryphans of the present invention are useful as anticonvulsant or neuroprotective agents.

8 Claims, No Drawings

CONTRYPHAN PEPTIDES

CROSS-REFERENCE TO RELATED APPLICATION

This application is a divisional of Ser. No. 09/061,026, filed Apr. 16, 1998, which is related to provisional application Ser. No. 60/068,737, filed Dec. 24, 1997, both of which are incorporated herein by reference.

This invention was made with Government support under Grant No. GM48677 awarded by the National Institute of General Medical Sciences, National Institutes of Health, Bethesda, Md. The United States Government has certain rights in the invention.

BACKGROUND OF THE INVENTION

This invention relates to relatively short peptides about 6–12 residues in length, which are naturally available in minute amounts in the venom of the cone snails or analogous to the naturally available peptides, and which include one or more D-tryptophan or D-leucine residues.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Mollusks of the genus Conus produce a highly toxic venom that enables them to carry out their unique predatory lifestyle. Prey are immobilized by the venom that is injected by means of a highly specialized venom apparatus, a disposable hollow tooth that functions both in the manner of a harpoon and a hypodermic needle.

Few interactions between organisms are more striking than those between a venomous animal and its envenomated victim. Venom may be used as a primary weapon to capture prey or as a defense mechanism. These venoms disrupt essential organ systems in the envenomated animal, and many of these venoms contain molecules directed to receptors and ion channels of neuromuscular systems.

The predatory cone snails (Conus) have developed a unique biological strategy. Their venom contains relatively small peptides that are targeted to various neuromuscular receptors and may be equivalent in their pharmacological diversity to the alkaloids of plants or secondary metabolites of microorganisms. Many of these peptides are among the smallest nucleic acid-encoded translation products having defined conformations, and as such, they are somewhat unusual. Peptides in this size range normally equilibrate among many conformations. Proteins having a fixed conformation are generally much larger.

The cone snails that produce these toxic peptides, which are generally referred to as conotoxins or conotoxin peptides, are a large genus of venomous gastropods comprising approximately 500 species. All cone snail species are predators that inject venom to capture prey, and the spectrum of animals that the genus as a whole can envenomate is broad. A wide variety of hunting strategies are used, however, every Conus species uses fundamentally the same basic pattern of envenomation.

Several peptides isolated from Conus venoms have been characterized. These include the α-, μ- and ω-which target nicotinic acetylcholine receptors, muscle sodium channels, and neuronal calcium channels, respectively (Olivera et al., 1985). Conopressins, which are vasopressin analogs, have also been identified (Cruz et al. 1987). In addition, peptides named conantokins have been isolated from the Conus geographus and Conus tutipa (Mena et al., 1990; Haack et al., 1990). These peptides have unusual age-dependent physiological effects: they induce a sleep-like state in mice younger than two weeks and hyperactive behavior in mice older than 3 weeks (Haack et al., 1990).

The standard amino acids in polypeptides translated from genes are exclusively in the L-configuration. In recent years it has been established that D-amino acids can be post-translationally introduced into such polypeptides (Kriel, 1994). Several small peptides have been characterized which contain a D-amino acid. The first of these was dermorphin, a potent heptapeptide agonist of the m-opiate receptor from amphibian skin, discovered by Erspamer and co-workers (Monteccuchi et al., 1981). A number of other peptides from amphibian skin (including the deltorphins and bombinin-H) were also found to have a D-amino acid. The cDNAs encoding these peptides were characterized (Richter et al., 1987; Richter et al., 1990). The results demonstrated unequivocally the presence of mRNA encoding the peptide precursor, indicating that the D-amino acid was post-translationally formed from the corresponding L-isomer.

In addition to these vertebrate systems, small peptides with D-amino acids have also been described in invertebrate systems, primarily molluscs. An FRMFamide analog from the bivalve, $Mytilus$ $edulis$, which contains a D-leucine has been characterized (Fujisawa et al., 1992). Likewise, the land snail $Achatina$ $fulica$ has D-amino acid-containing small peptides, achatin-I and fulicin (Kamatani et al., 1989; Ohta et al., 1991). The cDNA encoding the precursor of fulicin was found to contain the usual L-Asn codon at the D-Asn position (Yasuda-Kamatani et al., 1995). Recently, the post-translational inversion of an amino acid was demonstrated in vitro for ω-agatoxin-IVB (also termed ω-agatoxin-TK), a Ca channel inhibitor from funnel web spider (Shikata et al., 1995). The peptide isomerase that preferentially acts on $Ser^{46}$ of the 48-amino acid peptide has been isolated and characterized.

Although there is no homology between vertebrate and invertebrate peptides (and the three molluscan peptides exhibit no sequence similarity), in every case the D-amino acid is found in the second position. This suggests that for small D-amino acid-containing peptides, the proteolytic event which generates the mature peptide and the post-translational enzymatic system which converts an L- to a D-amino acid work in combination to always generate the D-amino acid at position 2.

Epilepsy is a recurrent paroxysmal disorder of cerebral function characterized by sudden brief attacks of altered consciousness, motor activity, sensory phenomena or inappropriate behavior caused by abnormal excessive discharge of cerebral neurons. Convulsive seizures, the most common form of attacks, begin with loss of consciousness and motor control, and tonic or clonic jerking of all extremities, but any recurrent seizure pattern may be termed epilepsy. The term primary or idiopathic epilepsy denotes those cases where no cause for the seizures can be identified. Secondary or symptomatic epilepsy designates the disorder when it is associated with such factors as trauma, neoplasm, infection, developmental abnormalities, cerebrovascular disease, or various metabolic conditions. Epileptic seizures are classified as partial seizures (focal, local seizures) or generalized seizures (convulsive or nonconvulsive). Classes of partial seizures include simple partial seizures, complex partial seizures and partial seizures secondarily generalized. Classes of generalized seizures include absence seizures, atypical absence seizures, myoclonic seizures, clonic seizures, tonic seizures, tonic-clonic seizures (grand mal) and atonic seizures. Therapeutics having anticonvulsant properties are used in the treatment of seizures. Most therapeutics used to abolish or attenuate seizures demonstrate activity at least through effects that reduce the spread of excitation from seizure foci and prevent detonation and disruption of function of normal aggregates of neurons. Anticonvulsants which have been utilized include phenytoin, phenobarbital, primidone, carbamazepine, ethosuximide, clonazepam and valproate. For further details of seizures and their therapy (see Rall & Schleifer (1985) and *The Merck Manual* (1992)).

It has been shown that neurotransmission mediated through the NMDA receptor complex is associated with seizures (Bowyer, 1982; MeNamara et al., 1988), ischemic neuronal injury (Simon et al., 1984; Park et al., 1988) and other phenomena including a synaptogenesis (Cline et al., 1987), spatial learning (Morris et al., 1986) and long-term potenitiation (Collinridge et al., 1983; Harris et al., 1984; Morris et al. , 1986). Regulation of these neuronal mechanisms by NMDA-mediated processes may involve activation of a receptor-gated calcium ion channel (Nowak et al., 1984; Mayer et al., 1987; Ascher and Nowak, 1988).

The NMDA channel is regulated by glycine. This amino acid increases NMDA-evoked currents in various tissues (Johnson and Ascher, 1987; Kleckner and Dingledine, 1988) by increasing the opening frequency of the NMDA channel (Johnson and Ascher, 1987). Thus, NMDA-induced calcium influx and intracellular accumulation through may be stimulted by glycine (Reynolds et al., 1987; Wroblewski et al., 1989), which interacts with its own distinct site (Williams et al., 1991). Furthermore, accumulation of intracellular calcium may be implicated in the aforementioned neuropathologies.

It is desired to identify additional peptides which target the NMDA receptor. It is further desired to identify compounds which are useful as anticonvulsant or neuroprptective agents.

SUMMARY OF THE INVENTION

The present invention is directed to contryphan peptides haing 6–12 amino acids, preferably including one or more D-tryptophan or D- leucinc residues. The peptides of the present invention are generically termed "contryphans," although the D-leucine containiig contryphlans are sometimes referred to as leu-contryphans. More specifically, the present invention is directed to contryphan peptides having the general formula $Xaa_1$-Cys-$Xaa_2$-$Xaa_3$-$Xaa_4$,-Pro-$Xaa_5$-Cys (SEQ ID NO:1), wherein $Xaa_1$ is any amino acid or des-$Xaa_1$, $Xaa_2$ is Pro, 4-trans-hydroxyproline or Val, $Xaa_3$ is D-Trp, L-Trp, D-Leu or L-Leu, preferably D-Trp or D-Leu, $Xaa_4$ is any amino acid and $Xaa_5$ is Trp or Tyr. When the peptide contains $Xaa_1$, it is preferably Gly, Glu, or Lys, most preferably Gly. When $Xaa_3$ is D- or L-Trp, $Xaa_2$ is preferably Pro or 4-trans-hydroxyroline. When $Xaa_3$ is D- or L-Leu, $Xaa_2$ is preferably Val. The carboxy terminus may contain a carboxyl or an amide, preferably an amide.

The present invention is further directed to the specific contryphan peptides as described herein. The present invention is also directed to nucleic acids encoding the contryphan peptides and their propeptides as described herein.

SUMMARY OF THE SEQUENCE LISTING

SEQ ID NO:1 is the generic contryphan sequence. SEQ ID NO:2 is the sequence for *C. stercusmuscarum* contryphan. SEQ ID NO:3 is the sequence for *C. purpurascens* contryphan-1. SEQ ID NO:4 is the sequence for *C. textile* contryphan-1. SEQ ID NO:5 is the sequence for *C. textile* contryphan-2. SEQ ID NO:6 is the sequence for *C. textile* contryphan-3. SEQ ID NO:7 is the sequence for *C. marmoreus* contryphan. SEQ ID NO:8 is the sequence for *C. purpurascens* contryphan-2or Leu-contryphan. SEQ ID NO:9 is the cDNA sequences for propetide of the *C. stercusmuscarum* contryphan. SEQ ID NO:10 is the propetide sequence of the *C. stercusmuscarum* contryphan. SEQ ID NO:11 is the cDNA sequence for propetide of the *C. purpurascens* contryphan-1. SEQ ID NO:12 is the propetide sequence of the *C. purpurascens* contryphan-1. SEQ ID NO:13 is the cDNA sequence for propetide of the *C. textile* contryphan-1. SEQ ID NO:14 is the propetide sequence of the *C. textile* contryphan-1. SEQ ID NO:15 is the cDNA sequence for propetide of the *C. textile* contryphan-2. SEQ ID NO:16 is the propetide sequence of the *C. textile* contryphan-2. SEQ ID NO:17 is the cDNA sequence for propetide of the *C. textile contryphan*-3. SEQ ID NO:18 is the propetide sequence of the *C. textile* contryphan-3. SEQ ID NO:19 is the cDNA sequence for propetide of the *C. marinoreus* contryphan. SEQ ID NO:20 is the propetide sequence of the *C. manmoreus* contryphan. SEQ ID NO:21 is the cDNA sequence for propetide of the *C. radiatus* contryphan. SEQ ID NO:22 is the propetide sequence of the *C. radiatus* contryphan. SEQ ID NO:23 is the sequence for *C. radiatus* contryphan. SEQ ID NO:24 is the sequence of a primer based on the signal sequence of a contryphan prepropeptide. SEQ ID NO:25 is the sequence of a primer based on the 3'-untranslated region of a contryphian prepropepitide. SEQ ID NO:26 is the sequence of a primer corresponding to the poly-A region of a contryphan. SEQ ID NO:27 is the sequence of a sequencing primer. SEQ ID NO:28 is the sequence of an oligonucleotide for colony hybridization. SEQ ID NO:29 is the sequence of a sequencing oligonucleotide.

DETAILED DESCRIPTION OF THE PREFERRED EMBODIMENT

The present invention is directed to contryphan peptides having 6–12 amino acids, preferably including one or more D-tryptophan or D- leucine residues. The peptides of the present invention are generically termed "contryphans," although the D-leucine containing contryphans are sometimes referred to as leu-contryphans. More specifically, the present invention is directed to contryphan peptides having the general formula $Xaa_1$-Cys-$Xaa_2$-$Xaa_3$-$Xaa_4$-Pro-$Xaa_5$-Cys (SEQ ID NO:1), wherein $Xaa_1$ is any amino acid or des-$Xaa_1$, $Xaa_2$ is Pro, 4-trans-hydroxyproline or Val, $Xaa_3$ is D-Trp, L-Trp, D-Leu or L-Leu, preferably D-Trp or D-Leu, $Xaa_4$ is any amino acid and $Xaa_5$ is Trp or Tyr. When the peptide contains $Xaa_1$, it is preferably Gly, Glu, or Lys, most preferably Gly. When $Xaa_3$ is D- or L-Trp, $Xaa_2$ is preferably Pro or 4-trans-hydroxyproline. When $Xaa_3$ is D- or L-Leu, $Xaa_2$ is preferably Val. The carboxy terminus may contain a carboxyl or an amide, preferably an amide.

The present invention is further directed to specific contryphan peptides as set forth in Table 1 and to nucleic acids encoding the contryphan peptides and their propeptides as identified and/or set forth in Table 2.

TABLE 1

Contryphan Peptides

| Conus sp. | Sequence | SEQ ID NO: |
|---|---|---|
| C. stercusmuscarum | GCX₁X₂QPWC | 2 |
| C. purpurascens con1 | GCX₁X₂DPWC | 3 |
| C. textile con1 | GCX₁X₂QYWC | 4 |
| C. textile con2 | KCVX₃YPWC | 5 |
| C. textile con3 | GCX₁X₂EPWC | 6 |
| C. marmoreus | ECX₁X₂HPWC | 7 |
| C. purpurascens con2 (L-con) | GCVX₃LPWC | 8 |

$X_1$ is Pro or 4-trans-hydroxyproline; $X_2$ is D-Trp or L-Trp, preferably D-Trp; $X_3$ is D-Leu or L-Leu, preferably D-Leu. The toxin may optionally contain a G at the C-terminus, or the C may contain a carboxyl or an amide group.

TABLE 2

Contryphan Propeptides

| Conus sp. | Propeptide Sequence | Propeptide (Nucleic Acid) SEQ ID NO: |
|---|---|---|
| C. stercusmuscarum | MGKLTILVLVAAVLLSTQVMVQGDADQPADRDAVPRDDNPSGTDGKFMNVLRRFGCPWQPWCG | 10 (9) |
| C. purpurascens con 1 | MGKLTILVLVAAVLLSTQVMVQGDGDQPAYRNAAPRDDNPGGAIGKFMNVLRRSGCPWDPWCG | 12 (11) |
| C. textile con 1 | MGKLTILVLVAVALLSTQVMVQGDGDQPADRDAVPRDDNPGGMSEKFLNALQRRGCPWQPYCG | 14 (13) |
| C. textile con 2 | MGKLTILVLVAAVLLSAQVMVQGDGDQPADRKAVPREDNPGGASGKLMDVLRPKKCVLYPWCG | 16 (15) |
| C. textile con 3 | MGKLTILVLVAAVLLSTQAMAQGDGDQPAARNAVPRDDNPDGPSAKFMNVQRRSGCPWEPWCG | 18 (17) |
| C. marmoreus | MGKLTILVLVAAVLLSTQVMVQGDRDQPADRNAVPRDDNPGRARRKRMKVLNESECPWHPWCG | 20 (19) |
| C. radiatus | MGKLTILVLVAAVLLSAQVMVQGDGDQPADRNAVPRDDNPGGASGKFMNVLRRSGCPWEPWCG | 22 (21) |

The sequence for contryphan R from *C. radiatus* is GCX₁X₂EPWC, wherein X₁ is Pro or 4-hydroxyproline and X₂ is D-Trp or L-Trp, preferably D-Trp (SEQ ID NO: 23). The toxin may optionally contain a G at the C-terminus, or the C may contain a carboxyl or an amide group. This peptide is disclosed in PCT/US97/20534, incorporated herein by reference.

Additional peptides falling within the general formula can be made based on the peptides shown in Tables 1 or 2 by making analogs of these peptides or by making conservative substitutiions for the amino acid residues shown in Tables 1 or 2. Conservative substitutions are well known in the art and include, for example, the change of (or vice versa): alanine to serine; arginine to lysine; asparagine to glutamine or histidine; aspartate to glutamate; cysteine to serine; glycine to proline; isoleucine to leucine or valine; methionine to leucine or isoleucine; phenylalanine to tyrosine, leucine or methionine; serine to threonine; tryptophan to tyrosine.

The contryphans of the present invention are useful as anticonvulsant or neuroprotective agents.

The contryphans preferably have a D-tryptophan or D-leucine residue. This is the first report of D-leucine being formed through post-translational modification in the Conus snails. Furthermore, in contrast to all of the small D-amino acid-containing peptides previously reported, the contryphans isolated to date do not have the D-amino acid in position 2. Like most peptides found in Conus venoms, contryphan is crosslinked by a disulfide bond. The discovery and characterization of contryphan indicates that the modification system for converting L- to D-amino acids evolved in Conus venom ducts differs significantly from the post-translational isomerization of an L- to a D-amino acid previously described for all other small peptides in both vertebrate, and previously characterized molluscan systems. In addition, analysis of a cDNA clones for the contryphans disclosed herein, has shown that D-Trp or D-Leu is coded for by the standard codons for L-Trp or L-Leu, respectively.

These contryphans have anticonvulsant activity in Fringes audiogenic seizure susceptible mice and in syndrome-specific seizure animal models. The contryphans are useful as anticonvulsant agents, as neuroprotective agents, for managing pain and for treating neurodegenerative disorders, especially those resulting from an overstimulation of excitatory amino acid receptors. Thus, the contryphans of the present invention are useful for the treatment and alleviation of epilepsy and as a general anticonvulsant agent. The contryphans are also useful to reduce neurotoxic injury associated with conditions of hypoxia, anoxia or ischemia which typically follows stroke, cerebrovascular accident, brain or spinal chord trauma, myocardial infarct, physical trauma, drownings, suffocation, perinatal asphyxia, or hypoglycemic events. The contryphans are further useful for the treatment of Alzheimer's disease, senile dementia, Amyotrophic Lateral Sclerosis, Parkinson's disease, Huntington's disease, Down's Syndrome, Korsakoff's disease, schizophrenia, AIDS dementia, multi-infarct dementia, and neuronal damage associated with uncontrolled seizures. The contryphans are further useful in controlling pain and are effective in the treatment of migraine. They can be used prophylactically or to relieve the symptoms associated with a migraine episode.

These peptides are sufficiently small to be chemically synthesized. General chemical syntheses for preparing the foregoing contryphan peptides are described hereinafter, along with specific chemical synthesis of one contryphan and indications of biological activities of these synthetic products. Various ones of these contryphan peptides can also be obtained by isolation and purification from specific Conus species using the technique described in U.S. Pat. No. 4,447,356 (Olivera et al., 1984), the disclosure of which is incorporated herein by reference.

Although the contryphan peptides of the present invention can be obtained by purification from cone snails, because the amounts of contryphan peptides obtainable from individual snails are very small, the desired substantially pure contryphan peptides are best practically obtained in commercially valuable amounts by chemical synthesis using solid-phase strategy. For example, the yield from a single cone snail may be about 10 micrograms or less of contryphan peptide. By "substantially pure" is meant that the peptide is present in the substantial absence of other biological molecules of the same type; it is preferably present in an amount of at least about 85% purity and preferably at least about 95% purity. Chemical synthesis of biologically active contryphan peptides depends of course upon correct determination of the amino acid sequence.

The contryphan peptides can also be produced by recombinant DNA techniques well known in the art. Such techniques are described by Sambrook et al. (1979). Nucleic acid sequences coding for the contryphan peptides and contryphan propeptides can be isolated and cloned using conventional techniques. Alternatively, nucleic acid sequences coding for the contryphan peptides and contryphan propeptides can be synthesized on the basis of the amino acid sequences of the peptides and propeptides disclosed herein and the known degeneracy of the genetic code. The nucleic acids for the peptides and propeptides can be designed to achieve maximal expression in a given host system. The peptides produced in this mannet are isolated, reduced if necessary, and oxidized to form the correct disulfide bonds.

One method of forming disulfide bonds in the contryphan peptides of the present invention is the air oxidation of the linear peptides for prolonged periods under cold room temperatures or at room temperature. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. It is also found that the linear peptide, or the oxidized product having more than one fraction, can sometimes be used for in vivo administration because the cross-linking and/or rearrangement which occurs in vivo has been found to create the biologically potent contryphan molecule. However, because of the dilution resulting from the presence of other fractions of less biopotency, a somewhat higher dosage may be required.

The peptides are synthesized by a suitable method, such as by exclusively solid-phase techniques, by partial solid-phase techniques, by fragment condensation or by classical solution couplings.

In conventional solution phase peptide synthesis, the peptide chain can be prepared by a series of coupling reactions in which constituent amino acids are added to the growing peptide chain in the desired sequence. Use of various coupling reagents, e.g., dicyclohexylcarbodiimide (DCC) or diisopropylcarbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. No. 4,105,603 (Vale et al., 1978). The fragment condensation method of synthesis is exemplified in U.S. Pat. No. 3,972,859 (1976). Other available syntheses are exemplified by U.S. Pat. Nos. 3,842,067 (1974) and 3,862,925 (1975). The synthesis of peptides containing γ-carboxyglutamic acid residues is exemplified by Rivier et al. (1987), Nishiuchi et al. (1993) and Zhou et al. (1996).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or paramethylbenzhydrylamine (MBHA) resin. Preparation of the hydroxymethyl resin is described by Bodansky et al. (1966). Chloromethylated resins are commercially available from Bio Rad Laboratories (Richmond, Calif.) and from Lab. Systems, Inc. The preparation of such a resin is described by Stewart et al. (1969). BHA and MBHA resin supports are commercially available, and are generally used when the desired polypeptide being synthesized has an unsubstituted amide at the C-terminus. Thus, solid resin supports may be any of those known in the art, such as one having the formulae —O—$CH_2$-resin support, —NH—BHA resin support, or —NH—MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (Kornreich et al., 1986) can be used, or should still other groups than the free acid be desired at the C-terminus, it may be preferable to synthesize the peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in K. Horiki et al. (1978), using KF in dimethylformamide (DMF) at about 60° C. for 24 hours with stirring, when a peptide having free acid at the C-terminus is to be synthesized. Following the coupling of the Boc-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder & Lubke (1965).

After removal of the α-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC, DIC, HBTU, HATU, TBTU in the presence of hydroxybenzotriazole (HOBt) or HOAt).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke (1965) and Kapoor (1970).

Each protected amino acid or amino acid sequence is introduced into the solid-phase reactor in about a twofold or more excess, and the coupling may be carried out in a medium of dimethylformamide (DMF):$CH_2Cl_2$ (1:1) or in DMF or $CH_2Cl_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (1970). Coupling reactions can be performed automatically, as on a Beckman 990 automatic synthesizer, using a program such as that reported in Rivier et al. (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptido-resin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF) or TFA, followed by oxidation as described above. A suitable method for cyclization is the method described by Cartier et al. (1996).

The contryphans are antagonists of the NMDA receptor sites and are useful as anticonvulsant agents, as neuroprotective agents, for managing pain and for treating neurodegenerative disorders, especially those resulting from an overstimulation of excitatory amino acid receptors. Thus, the contryphans of the present invention are useful for the treatment and alleviation of epilepsy and as a general anticonvulsant agent. The use of contryphans in these conditions includes the administration of a contryphan in a therapeutically effective amount to patients in need of treatment. The contryphans can be used to treat the seizures to reduce their effects and to prevent seizures.

The contryphans are also useful to reduce neurotoxic injury associated with conditions of hypoxia, anoxia or ischemia which typically follows stroke, cerebrovascular accident, brain or spinal chord trauma, myocardial infarct, physical trauma, drownings, suffocation, perinatal asphyxia, or hypoglycemic events. To reduce neurotoxic injury, the contryphans should be administered to the patient within 24 hours of the onset of the hypoxic, anoxic or ischemic condition in order for the contryphans to effectively minimize the CNS damage which the patient will experience.

The contryphans are further useful for the treatment of Alzheimer's disease, senile dementia, Amyotrophic Lateral Sclerosis, Parkinson's disease, Huntington's disease, Down's Syndrome, Korsakoff's disease, schizophrenia, AIDS dementia, multi-infarct dementia, and neuronal damage associated with uncontrolled seizures. The administration of the contryphans to a patient experiencing such conditions will serve to either prevent the patient form experiencing further neurodegeneration or it will decrease the rate at which neurodegeneration occurs. The contryphans are further useful in controlling pain and are effective in the treatment of migraine. They can be used prophylactically or to relieve the symptoms associated with a migraine episode.

The anticonvulsant effects of contryphans have been demonstrated in animal models. In rodents, contryphans are effective against supramaximal tonic extension seizures produced by maximal electroshock and threshold seizures induced by s.c. pentylenetetrazol or picrotoxin. Contryphans are also effective against focal seizures induced by aluminum hydroxide injection into the pre- and post-central gyri of rhesus monkeys. Contryphans when administered to patients with refractory complex partial seizures may markedly reduced seizure frequency and severity. Moreover, the clinical utility of contryphans as a therapeutic agent for epilepsy may include generalized tonic-clonic and complex partial seizures.

Studies in laboratory animal models demonstrate the neuroprotectant properties of contryphans. Contryphans protect against hypoxic damage to the hippocampal slice in vitro. In neonate rats, contryphans reduce the size of cortical infarcts and amount of hippocampal necrosis following bilateral carotid ligation and hypoxia. The contryphans may also be effective anti-pain agents.

For newly diagnosed patients with a seizure disorder and patients with seizure disorders for whom changes in drugs are being made, a relatively low dosage of drug is started and increased over a week or so to a standard therapeutic dosage. After about a week at such dosage, blood levels are obtained to determine the patient's pharmacokinetic response and, if appropriate, whether the effective therapeutic level has been reached. If seizures continue, the daily dosage is increased by small increments as dosage rises above the usual. Once seizures are brought under control, the drug should be continued without interruption at least one seizure-free year. At that time, discontinuation of the drug should be considered, since about 50% of such patients will remain seizure free without drugs. Patients whose attacks initially were difficult to control, those who failed a therapy-free trial and those with important social reasons for avoiding seizures should be treated indefinitely.

Pharmaceutical compositions containing a compound of the present invention as the active ingredient can be prepared according to conventional pharmaceutical compounding techniques. See, for example, *Remington's Pharmaceutical Sciences,* 18th Ed. (1990, Mack Publishing Co., Easton, Pa.). Typically, an antagonistic amount of the active ingredient will be admixed with a pharmaceutically acceptable carrier. The carrier may take a wide variety of forms depending on the form of preparation desired for administration, e.g., intravenous, oral or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may dissolved in a pharmaceutical carrier and administered as either a solution of a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The contryphans can also be administered in a cell based delivery system in which a DNA sequence encoding a contryphan is introduced into cells designed for implantation in the body of the patient, especially in the spinal cord region. Suitable delivery systems are described in U.S. Pat. No. 5,550,050 and published PCT Application Nos. WO 92/19195, WO 94/25503, WO 95/01203, WO 95/05452, WO 96/02286, WO 96/02646, WO 96/40871, WO 96/40959 and WO 97/12635. The DNA sequence can be isolated from cDNA libraries using degenerate probes based on the sequences of the contryphans disclosed herein or amplified from these libraries using appropriate degenerate primers. Alternatively, suitable DNA sequences can be prepared synthetically for each of the disclosed contryphan on the basis of the disclosed sequences and the known genetic code.

The contryphans are administered in an amount sufficient to antagonize the effects of excitatory amino acids or other agonists upon the NMDA receptor complex. The dosage range at which these contryphans exhibit this antagonistic effect can vary widely depending upon the particular disease being treated, the severity of the patient's disease, the patient, the specific contryphan being administered, the route of administration and the presence of other underlying disease states within the patient. Typically the contryphans exhibit their therapeutic effect at a dosage range from about 0.015 mg/kg to about 200 mg/kg, preferably from about 0.02 mg/kg to about 100 mg/kg of the active ingredient, more preferably from about 0.03 mg/kg to about 75 mg/kg of the active ingredient, and most preferably from about 0.03 mg/kg to about 50 mg/kg of the active ingredient. A suitable dose can be administered in multiple sub-doses per day. Typically, a dose or sub-dose may contain from about 0.1 mg to about 500 mg of the active ingredient per unit dosage form. A more preferred dosage will contain from about 0.5 mg to about 100 mg of active ingredient per unit dosage form.

The present invention is described by reference to the following Examples, which are offered by way of illustration and are not intended to limit the invention in any manner. Standard techniques well known in the art or the techniques specifically described below were utilized.

EXAMPLE 1

*C. stercusmitscarum* Contryphan Experimental Procedures

Venom Ducts and Preparation of Venom Extract: Live specimens of *C. stercusmuscarum* were obtained from the Philippines, and venom ducts were dissected immediately after delivery. Crude venom was squeezed out of the venom ducts (Cruz et al., 1976), lyophilized and stored at −70° C. until use. The lyophilized venom (0.5 g) was extracted using 40% acetonitrile as described previously (Jimenez et al., 1996).

Peptide Purification: Two independent purifications of contryphan-Sm were carried out from the crude venom of *C. stercusmuscarum.* In the first purification, contryphan was a side fraction identified in the course of purifying a different Conus peptide from this venom; however, enough contryphan was obtained to yield a sequence that made it clear that this peptide was homologous to contryphan-R from *C. radiatus,* which was described previously (Jimenez et al., 1996). Based on the initial sequencing data, the peptide was chemically synthesized (see below). Additional native peptide was then repurified from crude venom to compare more carefully with the synthetic peptide.

The crude venom was applied to a preparative $C_{18}$ column (22 mm×250 mm, 300 Å pore size, 15 $\mu$ particle size), with a flow rate of 20 mL/min. The region containing the contryphan-Sm that had been identified from the previous purification was then applied to an analytical $C_{18}$ column (218TP54,4.6 mm×250 mm) at a flow rate of 1 mL/min, and the analytical HPLC repeated to remove contaminant peaks. Detector sensitivity was adjusted to maximize the signal-to-noise ratio. It was clear that the major conformer of contryphan-Sm remained highly contaminated by other peptides; therefore, the minor conformer was collected instead for sequencing. In this procedure, an extract from venom duct material was purified by preparative HPLC using a gradient of 0–90% acetonitrile (ACN) in 0.08% trifluoroacetic acid (TFA) during 50 min. The region around the 10 minute elution mark was further purified by analytical HPLC using a much shallower gradient of 13.5–39.5% acetonitrile in 0.08% TFA during 30 min and the peak at about the 15 minute elution mark was rerun on the same gradient. The material from the last eluting peak in the rerun corresponds to the later-eluting conformer of contryphan-Sm, which was re-run to produce a two-peak pattern identical with the synthetic peptide. This material was used for amino acid sequencing. All HPLC was done at a wavelength of 220 nm.

Peptide Sequencing: The purified peptide (0.5 nmol in ~300 mL HPLC effluent) was treated with 300 mL of 20 mM tris(2-carboxyethyl)phosphine in 0.17 M citrate, pH 3 for 30 min at 65 ° C. After Vydac $C_{18}$ analytical purification of the reduced peptide, 3 mL of 4-vinylpyridine was added to the effluent (~500 mL) and the mixture was incubated for 20 min at room temperature in the dark. The mixture was diluted with 0.1% TFA and again purified by HPLC under similar conditions.

The purified peptide was sequenced by automated Edman chemistry (Edman and Begg, 1967) on an Applied Biosystems 477A protein sequencer with a 120A analyzer (DNA/Peptide Facility, University of Utah). The 3-phenyl-2-thiohydantoin derivatives were identified by HPLC. Predicted masses for each sequence were verified by determining the molecular mass using laser desorption and electrospray mass spectrometry, for which we are grateful to Dr. Anthony Craig of the Salk Institute for Biological Studies.

Peptide Synthesis: The protected peptide was synthesized using standard Fmoc (N-(9-flourenyl)methoxycarbonyl) chemistry and couplings using equimolar amounts of amino acid derivatives, dicyclohexylcarbodiimide and hydroxy benzotriazole. After synthesis, the terminal Fmoc group was removed by treatment with piperidine/N-methylpyrrolidone (1:4 v/v). The peptide was cleaved from the resin by treatment with TFA/$H_2O$/1,2-ethanedithiol/phenol/thioanisole (90:5:2.5:7.5:5 by vol) for 2 h at room temperature. The mixture was filtered under vacuum into methyl t-butyl ether (MTBE) at −10° C. Linear peptide was collected by centrifugation at 5000 g for 5 min and washed twice with MTBE. The pellet was dissolved in 60% acetonitrile containing 0.092% TFA and applied to a Vydac CIR preparative column (22×250 mm). Elution was done at 20 mL/min using a 12–30% gradient of acetonitrile in 0.08% TFA for 30 min. The major peak corresponding to the peptide fraction was oxidized with 1 mM iodine in 5% TFA, 20% acetonitrile (Gray, 1993), and after 5 min, the reaction was quenched with a few drops of 1.0 M ascorbic acid. The oxidized peptide was purified by HPLC.

Bioassay: Biological activity was assayed by intracranial injection into Swiss Webster mice (11 days old). Aliquots (20–30 mL) of peptide in normal saline were injected using a 0.3-mL syringe with a 29-gauge needle. Each control mouse was injected with an equal volume of normal saline solution containing dissolved residue of lyophilized column buffer.

Peptide Conformation Analvsis: An aliquot of synthetic contryphan-Sm was incubated at 20° C. for 20 min to allow equilibration of the two conformers. The sample was run on analytical HPLC at 0° C. with a flow rate of 1 mL/min and a gradient of 0.9% rise in acetonitrile/min as described under "Peptide Purification." The two components were collected and kept on ice. After 20 min, an aliquot of the later-eluting component was rechromatographed using the same HPLC conditions as before. Similarly, an aliquot of the earlier-eluting component was re-injected after 60 min sitting on ice and run under the same HPLC conditions. Then, aliquots of the two components were sequentially incubated at 20° C. for 20 min and rechromatographed.

EXAMPLE 2

Purification of *C. stercusmuscarlim* Contryphan

A small peptide was purified from the venom of the fish-hunting cone snail *C. stercusmuscarum*. When injected intracranially into mice, the peptide caused the "stiff-tail syndrome" previously described for contryphan-R (Jimenez et al., 1996). Mass spectrometry ($MH^+$=989.3) yielded a value that was close, but not identical, to contryphan-R. The peptide purified from *C. stercusmuscarum* did not elute as a single, sharp peak under our standard HPLC conditions. However, on amino acid sequencing analysis, the purified material yielded the following sequence: Gly-Cys-Hyp-Trp-Gln-Pro-Trp-Cys-$NH_2$ (SEQ ID NO:2).

This sequence differs from that of contryphan-R by a single amino acid; in position 5, the Glu residue in contryphan-R is substituted by a Gln residue in the *C. stercusmuscarum* peptide. The results strongly suggested that the *C. stercusmitscarurn* peptide was a contryphan, and raised the possibility that, as in contryphan-R, the tryptophan in position 4 was in the D-conformation.

Thus, two octapeptides with the same sequence as the purified native peptide were synthesized, with tryptophan-4 in the D, as well as the L conformation. When the synthetic peptides were chromatographed, the L-tryptophan derivative did not co-migrate with native peptide under our standard HPLC conditions. The D-tryptophan derivative, however, did co-elute with the native peptide. These results suggest that, like contryphan-R, the *C. stercusmuscarum* peptide has a D-tryptophan residue at position 4 and a L-tryptophan at position 7. The synthetic D-Trp-containing peptide (15 nmol) was injected into mice as described above. A characteristic symptomatology involving a stiff tail syndrome, paralysis of extremities, circular motion and barrel-rolling was observed. The suite of symptoms observed corresponds to the effects of contryphan-R at comparable doses (Jimenez et al., 1996). Given the similarities in biological activity, and the presence of D-tryptophan in homologous loci in both peptides, the newly characterized peptide is designated contryphan-Sm, which is [$Gln^5$]-contryphan-R.

The native peptide did not give a single peak when analyzed by reverse-phase (RP)-HPLC under standard conditions (see Example 1). The same anomalous elution behavior was observed for the synthetic contryphan-Sm. The elution profile consisted of two peaks with an elevated plateau absorbance between the peaks. When the HPLC is performed at 0° C., the elevated baseline disappears. To confirm that the two peaks are the same peptide, the late-eluting minor peak was incubated both at 0° C. and at 20° C. for 20 min before chromatography at 0° C. In both cases, the early-eluting peak was also found in the HPLC analysis. The profile obtained was very similar to the profile obtained when the HPLC is performed at 0° C. with most of the late-eluting peak having been converted to the early-eluting major peak. Preincubation at 0° C. for 20 min gave a smaller amount converted. Likewise, the major early-eluting peak gave rise to a profile obtained when the HPLC is performed at 0° C. when preincubated for 1 h before chromatography, with more of the late-eluting peak after incubation at 20° C. than at 0° C. These results suggest two interconvertible states for contryphan-Sm with different HPLC elution properties.

EXAMPLE 3

Identification and Sequencing of Conus Contryphan cDNA

Five milligrams of venom duct RNAs from *C. purpurascens* (obtained from the Gulf of California) and *C. stercus-*

*muscarum* were annealed to 3 pmol of a poly(T) oligonucleotide, and cDNA was synthesized by avian myeloblastosis virus (AMV) reverse transcriptase (5 units; Promega, Madison, Wis. according to the manufacturer's suggested protocol). The resulting cDNA was used as a template for polymerase chain reaction (PCR) in ten 10-mL sealed capillary tubes using an Idaho Technology air thermocycler. For *C. purpurascens,* the PCR primers used correspond to the signal sequence and 3'-untranslated region of the contryphan prepropeptide (Jimenez et al, 1997) and were as follows:

DHOG 552: 5' ATGGGGAAACTGACAATACTGG 3' (SEQ ID NO:24) and

DHOG 579: 5' GGCTGTCATWCGAATCGTGGA 3' (SEQ ID NO:25).

For *C. stercusmuscarum,* the second primer used corresponds to the poly(A) region and was DHOG 496: 5' GGCTTTTTTTTTTTTTTTTTTTTTTTTTTTTTT 3' (SEQ ID NO:26). Each reaction contained 50 ng template EDNA, 5 pmol each of the primers, 5 nmol of each of the four dNTPs and 0.5 units of Taq polymerase (Boehringer Mannheim, Indianapolis, Ind. ) in a buffer consisting of 50 mM Tris, pH 8.3, 250 mg/mL bovine serum albumin (BSA) and 2 mM $MgCl_2$. The PCR consisted of 40 cycles (94° C. pulse; 54° C. pulse; and 72° C., 15 sec).

The PCR product was gel-purified and recovered from agarose using the Bio-Rad Prep-A-Gene kit according to the manufacturer's protocol. The eluted DNA fragment was ligated to HincII (BRL)-digested pUC plasmid pTZ19U by first generating blunt ends. The purified PCR product (110 ng) was mixed with HincII-digested pTZ19U DNA (100 ng) and 0.2 mM each of the four dNTPs in a buffer containing 25 mM Tris HCl, pH 7.4, 5 mM $MgCl_2$, 5 mM dithiothreitol, 0.25 mM spermidine, 1 mM ATP, 1.25 mM hexamine cobalt chloride and 10 mg/mL BSA in a final volume of 18 mL. Two units of Large Fragment DNA Polymerase I (Klenow) were added, and the reaction was incubated for 15 min at 37° C. Ligation was carried out in the above-mentioned reaction mixture to which 5 units of T4 Ligase (Boehringer Mannheim) was added at 14° C. overnight.

Competent DH5a cells (0.1 mL; BRL) were transformed with the entire ligation mixture and spread on B agar plates (X-gal and isopropylthiogalactoside) containing 50 mg/mL of ampicillin (all from Sigma Chemical Co., St. Louis, Mo.). After incubation overnight at 37° C., colorless colonies produced by recombinant plasmids were screened for the presence of the correctly sized insert via PCR with vector-targeting primers in an Idaho Technology air thermocycler. Colonies that contained the correctly sized inserts were prepared for DNA sequencing.

Single-stranded DNA was prepared from putative contryphan clones for sequencing by PCR amplification of 50 ng of plasmid with a pair of vector primers, one of which was biotinylated, and for binding the resulting PCR product to streptavidin-bound magnetic polystyrene beads (DYNAL, Dynabeads M-280 Streptavidin). Material for solid-phase sequencing was prepared according to the manufacturer's suggested protocol, generating single-stranded nucleic acid which was sequenced using the Sequenase version 2.0 DNA sequencing kit, the nonbiotinylated vector primer and $^{35}S$ dATP, according to standard Sequenase protocol. The following oligonucleotide was used for sequencing:

DHOG 131: 5' CACACAGGAAACAGCTATG 3' (SEQ ID NO:27).

The prepropeptide structure of contryphan-R was previously described (Jimenez et al., 1996). The signal sequence and 3'-untranslated sequence of the contryphan-R precursor cDNA was used to do a PCR analysis of the venom of several fish-hunting cone snails. Because we had purified contryphan-Sm, we expected that reverse transcriptase (RT)-PCR of mRNA from the venom duct of C. stercusmuscarum would yield the precursor structure of contryphan-Sm. We did in fact isolate a PCR product, and an analysis of the RT-PCR clone gave the sequence identified in Table 2, above, i.e., the sequence shown in SEQ ID NO:9.

To determine whether other fish-hunting cone snails had contryphans, we analyzed a fish-hunting cone snail that we believe has long been isolated from the Indo-Pacific fish-hunting cone species: *C. purpitrascens,* from the eastern Pacific marine province. Using the same PCR primers described above, a cDNA clone was identified which has the nucleotide sequence identified in Table 2, above, i.e., the sequence shown in SEQ ID NO: 11. The C-terminal end of the only significant open reading frame encodes an octapeptide that is clearly homologous to contryphan-R and contryphan Sm; we refer to the predicted peptide as contryphan-P.

The three open reading frames which are the precursor structure of contryphan-R, contryphan-Sm and contryphan-P are compared in Table 2, above. In the mature peptide region, the three sequences only differ at position 5 of the mature octapeptide, as shown in Table 1, above. Glu-5 in contryphan-R is replaced by Gln in contryphan-Sm, and by Asp in contryphan-P. However, several amino acid changes are seen in the prepropeptide region of the precursors.

These results suggest that the contryphan family of peptides is likely to be found widely among fish-hunting cone snails. Although we have not done an extensive analysis of non-fish-hunting Conus, we did attempt to obtain a RT-PCR product from the venom duct of *Conus imperialis,* because a bromo tryptophan-containing heptapeptide was previously isolated from this worm-hunting snail. However, we did not obtain a PCR product under conditions that gave us clearly positive results when investigating venom ducts from *C. stercsismuscarum* and *C. purplirascens.* This result suggests that, even if there were members of the contryphan family present in *C. imperialis* venom ducts, the precursor sequence is sufficiently divergent so that it is not detected by the PCR procedure described in this Example.

EXAMPLE 4

Cloning of Additional Contryphans

In accordance with the procedures set forth in Example 3, additional contryphan cDNAs were cloned from *C. textile* and *C. marmoreus.* In addition, the clone for contryphan-R from *C. radiatus* was obtained by colony hybridization using the mixed oligomer DHOG 550 and sequenced using the oligonucleotides DHOG 399 and DHOG 550:

DHOG 550: 5' -CCRCACCANGGYTCCCA-3' (SEQ ID NO:28);

DHOG 399: 5' -TTGCATGCCTGCAGGTCGACT-3' (SEQ ID NO:29).

Three clones were obtained for *C. textile.* Th clones were sequenced as described in Example 3. The cDNA sequences are identified in Table 2 and set forth in SEQ ID NOs: 13, 15, 17, 19 and 21. The sequences of the precursor peptides are set forth in Table 2, above. The sequence of the mature toxins are set forth in Table 1, above. The sequences of two of the *C. textile* contryphans (designated *C. textile* con1 and *C. textile* con3) and the *C. marmoreus* contryphan contain D-Trp at position 4. The sequence of the third *C. textile* contryphan (designated *C. textile* con2) contains a D-Leu at position 4. The presence of the D-Leu was confirmed for an additional *C. purpurascens* contryphan as shown in the following Examples. The D-Leu containing contryphans, are termed Leu-contryphans.

EXAMPLE 5

*C. purvurascens* Leu-Contryphan Experimental Procedures

Specimen Collection and Venom Extraction: Specimens of the purple cone, *C. purpurascens,* were collected from the Clipperton Islands in the eastern Pacific. The venom was acquired by milking snails kept in aquaria. The snails were milked twice a week and milked venom was stored at −70° C. The venom from ~70 milkings was pooled for large-scale purification.

Reversed-Phase High Performance Liquid Chromatography (HPLC): All chromatography was done using Vydac $C_{18}$ columns as follows: preparative columns (22 mm×25 cm, 15 μ particle size, 300 Å pore size) or analytical columns (4.6 mm×25 cm, 5 μ particle size, #218TP54). HPLC buffers consisted of 0.1% TFA in water (A buffer), 0.092% TFA in 60% ACN in water (B buffer) and 0.08% TFA and 90% ACN in water (90% B buffer).

Purification of Natural Peptide by HPLC: Preparative scale reversed-phase HPLC was used as the first step in the purification of the milked venom. The venom was diluted with 0.1% TFA, applied to a preparative HPLC column with a guard column (22×50.8 mm) and eluted on a 0–100% gradient of 90% B buffer over 100 min (flow rate 20 ml/min). The crude fractions from preparative purification were further purified on an analytical HPLC column using slightly shorter gradients and a 1% B buffer increase per min.

Sequence Analysis: Purified, natural peptide was reduced with tris-(2-carboxyethyl-phosphine), HPLC-purified and then alkylated with 4-vinyl pyridine as described by Gray (1993). The pyridylethylated peptide was repurified by HPLC, and a sample analyzed by automated Edman degradation on an ABE 477A sequencer.

Mass Spectometry: Positive ion LSIMS spectra were obtained with and a JEOL JMS HX110 double-focusing spectrometer, fitted with and a cesium ion gun operated at +30 KV. Electrospray mass spectrometry was performed at the University of Utah Core Facility.

Peptide Svnthesis: Contryphan-P was synthesized with either L- or D-tryptophan in position 4. Leu-contryphan was synthesized with either L- or D-leucine in position 4, and each of these peptides was synthesized on both Rink amide and Wang-glycine resin to produce both the amidated and free carboxyl versions of the peptides. Leu-contryphan cysteines were acm-protected. The protected resin was synthesized using Fmoc (N-(9-methylflourenyl)methoxycarbonyl) chemistry and couplings using equimolar amounts of amino acid derivatives dicyclohexylcarbodidimide and hydroxybenzotrizole. At the completion of synthesis, the terminal Fmoc group was removed in situ by treatment with 20% piperidine in N-methylpyrrolidone.

Linear Leu-contryphan did not precipitate when cleavage mixture was filtered into MTBE; an alternative protocol was therefore used to isolate the linear peptide. The peptide was cleaved from the resin by treatment with TFA:water:1,2-ethanediol (94:5:1 by vol) for 1.5 hr at room temperature. The mixture was filtered under vacuum into 30 mo of 20% ACN containing 3% TFA and applied onto and a preparative column. Elution was done at 20 ml/min using and a gradient of ACN in 0.08% TFA. The major peak corresponding to the peptide fraction was oxidized with 1 mM iodine in 0.1% TFA in 20% ACN. The reactions was quenched with and a few drops of 0.1 M ascorbic acid. The oxidized peptide was purified by HPLC. Co-injection of an aliquot of natural peptide with synthetic peptides containing L-leucine or D-leucine at position 4 was done.

Bioassay: Biological activity was measured by intracranial injection in Swiss Webster mice (10 days old) and injection into the anterior region of the ventral fin of fish (0.7 g–0.9 g). Aliquots (25 μL for a mouse and 5 ViL for and a fish) of peptide in normal saline were injected using 0.3 ml syringe with and a 29-gauge needle. Each control mouse or fish was injected with normal saline solution containing dissolved residue of lyophilized columnn buffer. After injection, the mice were placed in cages and the fish in aquarium water for observation.

EXAMPLE 6

Purification of *C. purvurascens* Leu-Contryphan

Venom was obtained from Clipperton Island specimens of *C. purpurascens* by milking aquarium-maintained snails as described. Because specimen collection from this extremely isolated and uninhabited locality occurs most infrequently, only small amounts of venom were available and peptides were individually purified without assay, and a peptide was purified, sequenced and found to have considerable homology to contryphans, but diverges greatly from all contryphans previously isolated. The contryphan from the Clipperton Island *C. purpurascens,* in contrast to the contryphan identified in *C. purpurascens* from the Gulf of California and many other contryphans does not have and a tryptophan residue in the number 4 position. In these other contryphans, this tryptophan residue is in the D-configuration, and a unique characteristic of previously characterized members of this peptide family.

In order to ascertain the structure of the Clipperton contryphan peptide, it was chemically synthesized. Since L-Trp in position 4 was epimerized to D-Trp in other contryphans, both the D and L isomers of leucine were introduced at position 4 of the Clipperton contryphan peptide, and both peptides were synthesized in the amidated and free carboxyl form at the C-terminus. The four resulting synthetic peptide isomers were co-eluted with the native peptide. It was found that it is the D-leucine-containing synthetic peptide with and a free carboxyl group which co-migrates with native peptide, and that the amidated and the L-leucine forms of the peptide are resolved from the native material. Thus, the sequence of the C. purpurascens Leu-contryphan (con2) is Gly-Cys-Val-D-Leu-Leu-Pro-Trp-Cys (SEQ ID NO:8).

The peptide was tested for biological activity. Leu-contryphan appears to be less potent than the other contryphans when tested for producing the "stiff-tail" syndrome. However, when injected into fish, the secretion of mucous-like material from the fish skin was observed, symptomatology not observed for other peptides or other contryphans.

EXAMPLE 7

In vivo Activity of Contryphans in Frings Audiogenic Seizure Susceptible Mice In vivo anticonvulsant activity of the contryphans described above are analyzed in Frings audiogenic seizure susceptible mice as described by White et al. (1992). The contryphans demonstrate anticonvulsant activity in this model.

EXAMPLE 8

In vivo Activity of Contryphans in CF No. 1 Mice

In vivo anticonvulsant activity of the contryphans described above are analyzed in CF No. 1 mice as described by White et al. (1995), using the maximal electroshock, subcutaneous pentylenetetrazol (Metrazol) seizure threshold and threshold tonic extension test. The contryphans demonstrate anticonvulsant activity in this model.

It will be appreciated that the methods and compositions of the instant invention can be incorporated in the form of and a variety of embodiments, only and a few of which are disclosed herein. It will be apparent to the artisan that other embodiments exist and do not depart from the invention. Thus, the described embodiments are illustrative and should not be construed as restrictive.

LIST OF REFERENCES

Abiko, H. et al. (1986). Protective effect of phenytoin and enhancement of its action by combined administration of mannitol and vitamin E in cerebral ischemia. *Brain Res.* 38:328–335.

Aldrete, J. A. et al. (1979). Effect of pretreatment with thiopental and phenytoin on postischemic brain damage in rabbits. *Crit. Care Med.* 7:466–470.

Ascher, P. and Nowak, L. (1986). Calcium permeation of the channels activated by N-methyl-D-aspartate (NMDA) in mouse central neurons. *J. Physiol.* 377:35p.

Bodansky et al. (1966). *Chem. Ind.* 38:1597–98.

Bowyer, J. F. (1982). Phencyclidine inhibition of the rate of kindling development. *Esp. Neurol.* 75:173–175.

Cartier, G. E. et al. (1996). *J. Biol. Chem.* 271:7522–7528.

Chandler, P. et al. (1993). Polyamine-like Actions of Peptides Derived from Contryphan-G, an N-methyl-D-aspartate (NMDA) Antagonist. *J. Biol. Chem.* 268:17173–17178.

Cline, H. T. et al. (1987). N-Methyl-D-aspartate receptor antagonist desegregates eye-specific stripes. *Proc. Natl. Acad. Sci. USA* 84:4342–4345.

Collinridge, G. L. et al. (1983). Excitatory amino acids in synaptic transmission in the Schaffer collateral-commissural pathway of the rat hippocampus. *J. Physiol.* 334:34–46.

Cruz, L. J. et al. (1976). *Veliger* 18, 302–308

Cruz, L. J. et al. (1987). *Conus geographus* toxins that discriminate between neuronal and muscle sodium channels. *J. Biol. Chem.* 260:9280–9288.

Doyle, D. D. et al. (1993). Divalent cation competition with [$^3$H]saxitoxin binding to tetrodotoxin-resistant and -sensitive sodium channels. *J. Gen. Physiol.* 101:153–182.

Dudley, S. C. et al. (1995). A $\mu$-Conotoxin-Insensitive $Na^+$ Channel Mutant: Possible Localization of a Binding Site at the Outer Vestibule. *Biophys. J.* 69:1657–1665.

Edman, P. and Begg, G. (1967). *Eur. J. Biochem.* 1, 80–91

Fujisawa, I. et al. (1992). *Comp. Biochem. Physiol.* (C) 102, 91–95.

Gray, W. R. (1993). Disulfide Structures of Highly Bridged Peptides: A New Strategy for Analysis. *Protein Science* 2:1732–1748.

Haack, J. A. et al. (1990). Contryphan-T: a gamma-carboxyglutamate containing peptide with N-methyl-d-aspartate antagonist activity. *J. Biol. Chem.* 265:6025–6029.

Harris, E. W. et al. (1984). Long-term potentiation in the hippocampus involves activation of N-methyl-D-aspartate receptors. *Brain Res.* 323:132–137.

Jimenez, E. C. et al. (1996). *J. Biol. Chem.* 281:28002–28005

Jimenez, E. C. et al. (1997). *Biochemistry* 36:989–994

Horiki, K. et al. (1978). *Chemistry Letters* 165–68.

Johnson, J. W. and Ascher, P. (1987). Glycine potentiates the NMDA response in cultured mouse brain neurons. *Nature* 325:529–531.

Kaiser et al. (1970). *Anal. Biochem.* 34:595.

Kamatani, Y. et al. (1989). *Biochem. Biophys. Res. Comm.* 160, 1015–1020

Kapoor (1970). *J. Pharm. Sci.* 59:1–27.

Kleckner, N. W. and Dingledine, R. D. (1988). Requirement for glycine inactivation of NMDA receptors expressed in Xenopus oocytes. *Science* 241:835–837.

Kornreich, W. D. et al. (1986). U.S. Pat. No. 4,569,967.

Kreil, G. (1994). *J. Biol. Chem.* 269:10967–10970.

Mayer, M. L. et al. (1987). Agonist- and voltage-gated calcium entry in cultured mouse spinal cord neurons under voltage clamp measured using arsenazo III. *J. Neurosci.* 7:3230–3244.

Mena, E. E. et al. (1990). Contryphan-G: a novel peptide antagonist to the N-methyl-D-aspartic acid (NMDA) receptor. *Neurosci. Lett.* 118:241–244.

McNamara, J. O. et al. (1988). Anticonvulsant and antiepileptogenic action of MK-801 in the kindling and electroshock models. *Neuropharmacology* 27:563–568.

*The Merck Manual of Diagnosis and Therapy,* 16 Ed., Berkow, R. et al., eds., Merck Research Laboratories, Rahway, N.J., pp. 1436–1445 (1992).

*Methoden der Organischen Chemie* (*Houben-Weyl*): *Synthese von Peptiden*, E. Wunsch (Ed.), Georg Thieme Verlag, Stuttgart, Ger. (1974).

Monteccuchi, P. C. et al. (1981). *Int. J. Pept. Prot. Res.* 17:275–283.

Morris, R. G. M. et al. (1986). Selective impairment and blockade of long-term potentiation by an N-methyl-D-aspartate receptor antagonist, AP5. *Nature* 319:774–776.

Nehlig, A. et al. (1990). Effects of phenobarbital in the developing rat brain. In *Neoatal Seizures*, Wasterlain, C. G. and Vertt, P. (eds.), Raven Press, New York, pp. 285–194.

Nishiuchi, Y. et al. (1993). Synthesis of gamma-carboxyglutamic acid-containing peptides by the Boc strategy. Int. *J. Pept. Protein Res.* 42:533–538.

Nowak, L. et al. (1984). Magnesium gates glutamic-activated channels in mouse central neurons. *Nature* 307:462–465.

Ohta, N. et al. (1991). *Biochem. Biophys. Res. Commun.* 178, 486–493

Olivera, B. M. et al. (1984). U.S. Pat. No. 4,447,356.

Olivera, B. M. et al. (1985). Peptide neurotoxins from fish-hunting cone snails. *Science* 230:1338.

Park, C. K. et al. (1988). The glutamate antagonist MK-801 reduces focal ischemia brain damage in the rat. *Ann. Neurol.* 24:543–551.

Rall T. W. and Schleifer, L. S. in *Goodman and Gilman's The Pharmacological Basis of Therapeutics*, Seventh Ed., Gilman, A. G. et al., eds., Macmillan Publishing Co., New York, pp. 446–472 (1985).

*Remington's Pharmaceutical Sciences*, 18th Ed., Mack Publishing Co., Easton, Pa. (1990).

Reynolds, I. J. et al. (1987). $^3$H-Labeled MK-801 binding to excitatory amino acid receptor complex from rat brain is enhance by glycine. *Proc. Natl. Acad. Sci. USA* 84:7744–7748.

Richter, K. et al. (1987). *Science* 238:200–202.

Richter, K. et al. (1990). *Proc. Natl. Acad Sci. USA* 87, 4836–4839.

Rivier, J. R. et al. (1978). *Biopolymers* 17:1927–38.

Rivier, J. R. et al. (1987). Total synthesis and further characterization of the gamma-carboxyglutamate-containing 'sleeper' peptide from *Conus geographies. Biochem.* 26:8508.

Sambrook, J. et al. (1979). *Molecular Cloning. A Laboratory Manual*, 2nd Ed., Cold Spring Harbor Laboratory, Cold Spring Harbor, N.Y.

Schroder & Lubke (1965). *The Peptides* 1:72–75, Academic Press, N.Y.

Shikata, Y. et al. (1995). *J. Biol. Chem.* 270, 16719–16723

Simon, R. P. et al. (1984). Blockade of N-methyl-D-aspartate receptors may protect against ischemic damage in the brain. *Science* 226:850–852.

Skolnick, P. et al. (1992). Noncompetitive Inhibition of N-Methyl-D-Aspartate by Contryphan-G: Evidence for an Allosteric Interaction at Polyamines Sites. *J. Neurochem.* 59:1526–1521.

Stewart and Young, *Solid-Phase Peptide Synthesis*, Freeman & Co., San Francisco, Calif. (1969).

Troupin, A. S. et al. (1986). MK-801. *In New Anticonvulsant Drugs, Current Problems in Epilepsy* 4, Meldrum, B. S. and Porter, R. J. (eds.), John Libbey, London, pp. 191–202.

Vale et al. (1978). U.S. Pat. No. 4,105,603.

White, H. S., et al. (1992). Anticonvulsant profile of MDL 27,266: an orally active, broad-spectrum anticonvulsant agent. *Epilepsy Res.* 12:217–226.

White, H. S., et al. (1995). Experimental Selection, Quantification, and Evaluation of Antiepileptic Drugs. *In Antiepileptic Drugs,* 4th Ed., Levy, R. H., eds., Raven Press, New York, pp. 99–110.

Williams, K. et al. (1991). Modulation of the NMDA receptor by polyamines (Minireview). *Life Sci.* 48:469–498.

Wong, E. H. P. et al. (1986). The anticonvulsant MK-801 is a potent NMDA antagonist. *Proc. Natl. Acad. Sci. USA* 83:7104–7108.

Yasuda-Kamiatani, Y. et al. (1995). *J. Neurochem.* 64,2248–2255

Zhou L. M., et al. (1996a). Synthetic Analogues of Contryplian-G: NMDA Antagonists Acting Through a Novel Polyamine-Coupled Site. *J. Neuroche* 66:620–628.

U.S. Pat. No. 3,972,859 (1976).

U.S. Pat. No. 3,842,067 (1974).

U.S. Pat. No. 3,862,925 (1975).

U.S. Pat. No. 5,550,050.

PCT Published Application WO 96/11698.

PCT Published Application No. WO 92/19195.

PCT Published Application No. WO 94/25503.

PCT Published Application No. WO 95/01203.

PCT Published Application No. WO 95/05452.

PCT Published Application No. WO 96/02286.

PCT Published Application No. WO 96/02646.

PCT Published Application No. WO 96/40871.

PCT Published Application No. WO 96/40959.

PCT Published Application No. WO 97/12635.

What is claimed is:

1. An isolated nucleic acid comprising a DNA sequence coding for a contryphan propeptide selected from the group consisting of:

(a) a propeptide having the amino acid sequence set forth in SEQ ID NO:10;

(b) a propeptide having the amino acid sequence set forth in SEQ ID NO:12;

(c) a propeptide having the amino acid sequence set forth in SEQ ID NO:14;

(d) a propeptide having the amino acid sequence set forth in SEQ ID NO:16;

(e) a propeptide having the amino acid sequence set forth in SEQ ID NO:18;

(f) a propeptide having the amino acid sequence set forth in SEQ ID NO:20; and (g) a propeptide having the amino acid sequence set forth in SEQ ID NO:22.

2. The nucleic acid of claim 1 having the DNA sequence set forth in SEQ ID NO:9.

3. The nucleic acid of claim 1 having the DNA sequence set forth in SEQ ID NO:11.

4. The nucleic acid of claim 1 having the DNA sequence set forth in SEQ ID NO:13.

5. The nucleic acid of claim 1 having the DNA sequence set forth in SEQ ID NO:15.

6. The nucleic acid of claim 1 having the DNA sequence set forth in SEQ ID NO:17.

7. The nucleic acid of claim 1 having the DNA sequence set forth in SEQ ID NO:19.

8. The nucleic acid of claim 1 having the DNA sequence set forth in SEQ ID NO:21.

* * * * *

SEQUENCE LISTING

```
(1) GENERAL INFORMATION:

   (iii) NUMBER OF SEQUENCES: 29


(2) INFORMATION FOR SEQ ID NO:1:

     (i) SEQUENCE CHARACTERISTICS:
          (A) LENGTH: 8 amino acids
          (B) TYPE: amino acid
          (C) STRANDEDNESS:
          (D) TOPOLOGY: linear

    (ii) MOLECULE TYPE: peptide

   (iii) HYPOTHETICAL: YES

    (ix) FEATURE:
          (A) NAME/KEY: Peptide
          (B) LOCATION: 1..4
          (D) OTHER INFORMATION: /note= "Xaa at postion 1 is any
               amino acid or des-Xaa; Xaa at position 3 is Pro,
               4-trans-hydroxy-Pro or Val; Xaa at position 4 is D- or
               L-Trp or D- or L-Leu. "

    (ix) FEATURE:
          (A) NAME/KEY: Peptide
          (B) LOCATION: 5..7
          (D) OTHER INFORMATION: /note= "Xaa at position 5 is any
               amino acid; Xaa at position 7 is Trp or Tyr."

    (xi) SEQUENCE DESCRIPTION: SEQ ID NO:1:

Xaa Cys Xaa Xaa Xaa Pro Xaa Cys
1               5


(2) INFORMATION FOR SEQ ID NO:2:

     (i) SEQUENCE CHARACTERISTICS:
```

-continued

```
        (A) LENGTH: 8 amino acids
        (B) TYPE: amino acid
        (C) STRANDEDNESS:
        (D) TOPOLOGY: linear

   (ii) MOLECULE TYPE: peptide

   (vi) ORIGINAL SOURCE:
        (A) ORGANISM: Conus stercusmuscarum

   (ix) FEATURE:
        (A) NAME/KEY: Peptide
        (B) LOCATION: 3..4
        (D) OTHER INFORMATION: /note= "Xaa at residue 3 is Pro or
             4-trans-hydroxyproline; Xaa at residue 4 is D-Trp or
             L-Trp."

   (xi) SEQUENCE DESCRIPTION: SEQ ID NO:2:

Gly Cys Xaa Xaa Gln Pro Trp Cys
1               5


(2) INFORMATION FOR SEQ ID NO:3:

    (i) SEQUENCE CHARACTERISTICS:
        (A) LENGTH: 8 amino acids
        (B) TYPE: amino acid
        (C) STRANDEDNESS:
        (D) TOPOLOGY: linear

   (ii) MOLECULE TYPE: peptide

   (vi) ORIGINAL SOURCE:
        (A) ORGANISM: Conus purpurascens

   (ix) FEATURE:
        (A) NAME/KEY: Peptide
        (B) LOCATION: 3..4
        (D) OTHER INFORMATION: /note= "Xaa at position 3 is Pro or
             4-trans=hydroxyproline; Xaa at position 4 is D-Trp or
             L-Trp."

   (xi) SEQUENCE DESCRIPTION: SEQ ID NO:3:

Gly Cys Xaa Xaa Asp Pro Trp Cys
1               5


(2) INFORMATION FOR SEQ ID NO:4:

    (i) SEQUENCE CHARACTERISTICS:
        (A) LENGTH: 8 amino acids
        (B) TYPE: amino acid
        (C) STRANDEDNESS:
        (D) TOPOLOGY: linear

   (ii) MOLECULE TYPE: peptide

   (vi) ORIGINAL SOURCE:
        (A) ORGANISM: Conus textile

   (ix) FEATURE:
        (A) NAME/KEY: Peptide
        (B) LOCATION: 3..4
        (D) OTHER INFORMATION: /note= "Xaa at position 3 is Pro or
             4-trans-hydroxyproline; Xaa at position 4 is D-Trp or
             L-Trp."

   (xi) SEQUENCE DESCRIPTION: SEQ ID NO:4:

Gly Cys Xaa Xaa Gln Tyr Trp Cys
1               5


(2) INFORMATION FOR SEQ ID NO:5:

    (i) SEQUENCE CHARACTERISTICS:
        (A) LENGTH: 8 amino acids
```

-continued (B) TYPE: amino acid
(C) STRANDEDNESS:
(D) TOPOLOGY: linear (ii) MOLECULE TYPE: peptide (vi) ORIGINAL SOURCE:
(A) ORGANISM: Conus textile (ix) FEATURE:
(A) NAME/KEY: Peptide
(B) LOCATION: 4
(D) OTHER INFORMATION: /note= "Xaa at position 4 is D-Leu or L-Leu."

(xi) SEQUENCE DESCRIPTION: SEQ ID NO:5:

```
Lys Cys Val Xaa Tyr Pro Trp Cys
1               5
```

(2) INFORMATION FOR SEQ ID NO:6:

(i) SEQUENCE CHARACTERISTICS:
(A) LENGTH: 8 amino acids
(B) TYPE: amino acid
(C) STRANDEDNESS:
(D) TOPOLOGY: linear (ii) MOLECULE TYPE: peptide (vi) ORIGINAL SOURCE:
(A) ORGANISM: Conus textile (ix) FEATURE:
(A) NAME/KEY: Peptide
(B) LOCATION: 3..4
(D) OTHER INFORMATION: /note= "Xaa at residue 3 is Pro or 4-trans-hydroxyproline; Xaa at residue 4 is D-Trp or L-Trp."

(xi) SEQUENCE DESCRIPTION: SEQ ID NO:6:

```
Gly Cys Xaa Xaa Glu Pro Trp Cys
1               5
```

(2) INFORMATION FOR SEQ ID NO:7:

(i) SEQUENCE CHARACTERISTICS:
(A) LENGTH: 8 amino acids
(B) TYPE: amino acid
(C) STRANDEDNESS:
(D) TOPOLOGY: linear (ii) MOLECULE TYPE: peptide (vi) ORIGINAL SOURCE:
(A) ORGANISM: Conus marmoreus (ix) FEATURE:
(A) NAME/KEY: Peptide
(B) LOCATION: 3..4
(D) OTHER INFORMATION: /note= "Xaa at residue 3 is Pro or 4-trans-hydroxyproline; Xaa at residue 4 is D-Trp or L-Trp."

(xi) SEQUENCE DESCRIPTION: SEQ ID NO:7:

```
Glu Cys Xaa Xaa His Pro Trp Cys
1               5
```

(2) INFORMATION FOR SEQ ID NO:8:

(i) SEQUENCE CHARACTERISTICS:
(A) LENGTH: 8 amino acids
(B) TYPE: amino acid
(C) STRANDEDNESS:

-continued (D) TOPOLOGY: linear (ii) MOLECULE TYPE: peptide (vi) ORIGINAL SOURCE:
(A) ORGANISM: Conus purpurascens (ix) FEATURE:
(A) NAME/KEY: Peptide
(B) LOCATION: 4
(D) OTHER INFORMATION: /note= "Xaa at residue 4 is D-Leu or L-Leu."

(xi) SEQUENCE DESCRIPTION: SEQ ID NO:8:

```
Gly Cys Val Xaa Leu Pro Trp Cys
1               5
```

(2) INFORMATION FOR SEQ ID NO:9:

(i) SEQUENCE CHARACTERISTICS:
(A) LENGTH: 291 base pairs
(B) TYPE: nucleic acid
(C) STRANDEDNESS: double
(D) TOPOLOGY: linear (ii) MOLECULE TYPE: cDNA (vi) ORIGINAL SOURCE:
(A) ORGANISM: Conus stercusmuscarum (ix) FEATURE:
(A) NAME/KEY: CDS
(B) LOCATION: 1..189

(xi) SEQUENCE DESCRIPTION: SEQ ID NO:9:

```
ATG GGG AAA CTG ACA ATA CTG GTT CTT GTT GCT GCT GTA CTG TTG TCG       48
Met Gly Lys Leu Thr Ile Leu Val Leu Val Ala Ala Val Leu Leu Ser
  1               5                  10                  15

ACC CAG GTC ATG GTT CAA GGT GAC GCA GAT CAA CCT GCA GAT CGT GAT       96
Thr Gln Val Met Val Gln Gly Asp Ala Asp Gln Pro Ala Asp Arg Asp
            20                  25                  30

GCA GTG CCA AGA GAC GAT AAC CCA AGT GGA ACG GAT GGA AAG TTC ATG      144
Ala Val Pro Arg Asp Asp Asn Pro Ser Gly Thr Asp Gly Lys Phe Met
        35                  40                  45

AAT GTT CTA CGT CGG TTT GGA TGT CCG TGG CAA CCT TGG TGT GGC          189
Asn Val Leu Arg Arg Phe Gly Cys Pro Trp Gln Pro Trp Cys Gly
    50                  55                  60

TGATCGGAAT CCACGATTGC TATGACAGCC AACAGTGCCG CACTGAATTA CCCTACAGTG    249

GTCTGGTTGC TCCAGAACAA TGATGGTTTG AAAACGTATT CG                       291
```

(2) INFORMATION FOR SEQ ID NO:10:

(i) SEQUENCE CHARACTERISTICS:
(A) LENGTH: 63 amino acids
(B) TYPE: amino acid
(D) TOPOLOGY: linear (ii) MOLECULE TYPE: protein (xi) SEQUENCE DESCRIPTION: SEQ ID NO:10:

```
Met Gly Lys Leu Thr Ile Leu Val Leu Val Ala Ala Val Leu Leu Ser
  1               5                  10                  15

Thr Gln Val Met Val Gln Gly Asp Ala Asp Gln Pro Ala Asp Arg Asp
            20                  25                  30

Ala Val Pro Arg Asp Asp Asn Pro Ser Gly Thr Asp Gly Lys Phe Met
        35                  40                  45
```

-continued

```
Asn Val Leu Arg Arg Phe Gly Cys Pro Trp Gln Pro Trp Cys Gly
     50                  55                  60
```

(2) INFORMATION FOR SEQ ID NO:11:

```
     (i) SEQUENCE CHARACTERISTICS:
          (A) LENGTH: 219 base pairs
          (B) TYPE: nucleic acid
          (C) STRANDEDNESS: double
          (D) TOPOLOGY: linear

    (ii) MOLECULE TYPE: cDNA

    (vi) ORIGINAL SOURCE:
          (A) ORGANISM: Conus purpurascens

    (ix) FEATURE:
          (A) NAME/KEY: CDS
          (B) LOCATION: 1..189

    (xi) SEQUENCE DESCRIPTION: SEQ ID NO:11:

ATG GGG AAA CTG ACA ATA CTG GTT CTT GTT GCT GCT GTA CTG TTG TCG        48
Met Gly Lys Leu Thr Ile Leu Val Leu Val Ala Ala Val Leu Leu Ser
     65                  70                  75

ACC CAG GTC ATG GTT CAA GGT GAC GGA GAT CAA CCG GCA TAT CGT AAT        96
Thr Gln Val Met Val Gln Gly Asp Gly Asp Gln Pro Ala Tyr Arg Asn
 80                  85                  90                  95

GCA GCG CCA AGA GAC GAT AAC CCA GGT GGA GCG ATT GGA AAG TTC ATG       144
Ala Ala Pro Arg Asp Asp Asn Pro Gly Gly Ala Ile Gly Lys Phe Met
                100                 105                 110

AAT GTT CTA CGT CGG TCT GGA TGT CCG TGG GAT CCT TGG TGT GGC           189
Asn Val Leu Arg Arg Ser Gly Cys Pro Trp Asp Pro Trp Cys Gly
            115                 120                 125

TGATTGGAAT CCACGATTGC AATGACAGCC                                      219
```

(2) INFORMATION FOR SEQ ID NO:12:

```
     (i) SEQUENCE CHARACTERISTICS:
          (A) LENGTH: 63 amino acids
          (B) TYPE: amino acid
          (D) TOPOLOGY: linear

    (ii) MOLECULE TYPE: protein

    (xi) SEQUENCE DESCRIPTION: SEQ ID NO:12:

Met Gly Lys Leu Thr Ile Leu Val Leu Val Ala Ala Val Leu Leu Ser
  1               5                  10                  15

Thr Gln Val Met Val Gln Gly Asp Gly Asp Gln Pro Ala Tyr Arg Asn
            20                  25                  30

Ala Ala Pro Arg Asp Asp Asn Pro Gly Gly Ala Ile Gly Lys Phe Met
        35                  40                  45

Asn Val Leu Arg Arg Ser Gly Cys Pro Trp Asp Pro Trp Cys Gly
     50                  55                  60
```

(2) INFORMATION FOR SEQ ID NO:13:

```
     (i) SEQUENCE CHARACTERISTICS:
          (A) LENGTH: 219 base pairs
          (B) TYPE: nucleic acid
          (C) STRANDEDNESS: double
          (D) TOPOLOGY: linear

    (ii) MOLECULE TYPE: cDNA

    (vi) ORIGINAL SOURCE:
          (A) ORGANISM: Conus textile
```

-continued

```
    (ix) FEATURE:
          (A) NAME/KEY: CDS
          (B) LOCATION: 1..189

    (xi) SEQUENCE DESCRIPTION: SEQ ID NO:13:

ATG GGG AAA CTG ACA ATA CTG GTT CTT GTT GCT GTT GCA CTG TTG TCG        48
Met Gly Lys Leu Thr Ile Leu Val Leu Val Ala Val Ala Leu Leu Ser
     65                  70                  75

ACC CAG GTC ATG GTT CAA GGT GAC GGA GAT CAA CCT GCA GAT CGT GAC        96
Thr Gln Val Met Val Gln Gly Asp Gly Asp Gln Pro Ala Asp Arg Asp
 80                  85                  90                  95

GCA GTG CCA AGA GAC GAT AAT CCA GGT GGA ATG AGT GAA AAG TTC TTG       144
Ala Val Pro Arg Asp Asp Asn Pro Gly Gly Met Ser Glu Lys Phe Leu
                100                 105                 110

AAT GCT CTG CAA AGA CGT GGA TGT CCG TGG CAA CCT TAT TGT GGC           189
Asn Ala Leu Gln Arg Arg Gly Cys Pro Trp Gln Pro Tyr Cys Gly
            115                 120                 125

TGATCAGAAT CCACGATTGC TATGACAGCC                                      219
```

```
(2) INFORMATION FOR SEQ ID NO:14:

     (i) SEQUENCE CHARACTERISTICS:
          (A) LENGTH: 63 amino acids
          (B) TYPE: amino acid
          (D) TOPOLOGY: linear

    (ii) MOLECULE TYPE: protein

    (xi) SEQUENCE DESCRIPTION: SEQ ID NO:14:

Met Gly Lys Leu Thr Ile Leu Val Leu Val Ala Val Ala Leu Leu Ser
  1               5                  10                  15

Thr Gln Val Met Val Gln Gly Asp Gly Asp Gln Pro Ala Asp Arg Asp
             20                  25                  30

Ala Val Pro Arg Asp Asp Asn Pro Gly Gly Met Ser Glu Lys Phe Leu
         35                  40                  45

Asn Ala Leu Gln Arg Arg Gly Cys Pro Trp Gln Pro Tyr Cys Gly
     50                  55                  60
```

```
(2) INFORMATION FOR SEQ ID NO:15:

     (i) SEQUENCE CHARACTERISTICS:
          (A) LENGTH: 219 base pairs
          (B) TYPE: nucleic acid
          (C) STRANDEDNESS: double
          (D) TOPOLOGY: linear

    (ii) MOLECULE TYPE: cDNA

    (vi) ORIGINAL SOURCE:
          (A) ORGANISM: Conus textile

    (ix) FEATURE:
          (A) NAME/KEY: CDS
          (B) LOCATION: 1..189

    (xi) SEQUENCE DESCRIPTION: SEQ ID NO:15:

ATG GGG AAA CTG ACA ATA CTG GTT CTT GTT GCT GCT GTC CTG TTG TCG        48
Met Gly Lys Leu Thr Ile Leu Val Leu Val Ala Ala Val Leu Leu Ser
     65                  70                  75

GCC CAG GTC ATG GTT CAA GGT GAC GGA GAT CAA CCT GCA GAT CGT AAA        96
Ala Gln Val Met Val Gln Gly Asp Gly Asp Gln Pro Ala Asp Arg Lys
 80                  85                  90                  95

GCA GTG CCA AGA GAG GAT AAC CCA GGT GGA GCG AGT GGA AAG CTC ATG       144
Ala Val Pro Arg Glu Asp Asn Pro Gly Gly Ala Ser Gly Lys Leu Met
                100                 105                 110
```

-continued

```
GAT GTT CTA CGT CCG AAA AAA TGT GTG TTG TAT CCT TGG TGT GGC          189
Asp Val Leu Arg Pro Lys Lys Cys Val Leu Tyr Pro Trp Cys Gly
            115                 120                 125

TGATCGGAAT CCACGATTGC AATGACAGCC                                     219
```

(2) INFORMATION FOR SEQ ID NO:16:

(i) SEQUENCE CHARACTERISTICS:
(A) LENGTH: 63 amino acids
(B) TYPE: amino acid
(D) TOPOLOGY: linear (ii) MOLECULE TYPE: protein (xi) SEQUENCE DESCRIPTION: SEQ ID NO:16:

```
Met Gly Lys Leu Thr Ile Leu Val Leu Val Ala Ala Val Leu Leu Ser
  1               5                  10                  15

Ala Gln Val Met Val Gln Gly Asp Gly Asp Gln Pro Ala Asp Arg Lys
             20                  25                  30

Ala Val Pro Arg Glu Asp Asn Pro Gly Gly Ala Ser Gly Lys Leu Met
         35                  40                  45

Asp Val Leu Arg Pro Lys Lys Cys Val Leu Tyr Pro Trp Cys Gly
     50                  55                  60
```

(2) INFORMATION FOR SEQ ID NO:17:

(i) SEQUENCE CHARACTERISTICS:
(A) LENGTH: 219 base pairs
(B) TYPE: nucleic acid
(C) STRANDEDNESS: double
(D) TOPOLOGY: linear (ii) MOLECULE TYPE: cDNA (vi) ORIGINAL SOURCE:
(A) ORGANISM: Conus textile (ix) FEATURE:
(A) NAME/KEY: CDS
(B) LOCATION: 1..189

(xi) SEQUENCE DESCRIPTION: SEQ ID NO:17:

```
ATG GGG AAA CTG ACA ATA CTG GTT CTT GTT GCT GCT GTA CTG TTG TCG       48
Met Gly Lys Leu Thr Ile Leu Val Leu Val Ala Ala Val Leu Leu Ser
     65                  70                  75

ACC CAG GCC ATG GCT CAA GGT GAC GGA GAC CAA CCT GCA GCC CGT AAT       96
Thr Gln Ala Met Ala Gln Gly Asp Gly Asp Gln Pro Ala Ala Arg Asn
 80                  85                  90                  95

GCA GTA CCA AGA GAC GAT AAC CCA GAT GGA CCG AGT GCA AAG TTC ATG      144
Ala Val Pro Arg Asp Asp Asn Pro Asp Gly Pro Ser Ala Lys Phe Met
                100                 105                 110

AAT GTT CAA CGT CGG TCT GGA TGT CCG TGG GAG CCG TGG TGT GGC          189
Asn Val Gln Arg Arg Ser Gly Cys Pro Trp Glu Pro Trp Cys Gly
            115                 120                 125

TAATCCGAAT CCACGATTGC TATGACAGCC                                     219
```

(2) INFORMATION FOR SEQ ID NO:18:

(i) SEQUENCE CHARACTERISTICS:
(A) LENGTH: 63 amino acids
(B) TYPE: amino acid
(D) TOPOLOGY: linear (ii) MOLECULE TYPE: protein -continued

```
    (xi) SEQUENCE DESCRIPTION: SEQ ID NO:18:

Met Gly Lys Leu Thr Ile Leu Val Leu Val Ala Ala Val Leu Leu Ser
  1             5                  10                  15

Thr Gln Ala Met Ala Gln Gly Asp Gly Asp Gln Pro Ala Ala Arg Asn
             20                  25                  30

Ala Val Pro Arg Asp Asp Asn Pro Asp Gly Pro Ser Ala Lys Phe Met
        35                  40                  45

Asn Val Gln Arg Arg Ser Gly Cys Pro Trp Glu Pro Trp Cys Gly
     50                  55                  60


(2) INFORMATION FOR SEQ ID NO:19:

     (i) SEQUENCE CHARACTERISTICS:
          (A) LENGTH: 219 base pairs
          (B) TYPE: nucleic acid
          (C) STRANDEDNESS: double
          (D) TOPOLOGY: linear

    (ii) MOLECULE TYPE: cDNA

    (vi) ORIGINAL SOURCE:
          (A) ORGANISM: Conus marmoreus

    (ix) FEATURE:
          (A) NAME/KEY: CDS
          (B) LOCATION: 1..189

    (xi) SEQUENCE DESCRIPTION: SEQ ID NO:19:

ATG GGG AAA CTG ACA ATA CTG GTT CTT GTT GCT GCT GTA CTC TTG TCG       48
Met Gly Lys Leu Thr Ile Leu Val Leu Val Ala Ala Val Leu Leu Ser
     65                  70                  75

ACC CAG GTC ATG GTT CAA GGT GAC AGA GAT CAA CCT GCA GAT CGT AAT       96
Thr Gln Val Met Val Gln Gly Asp Arg Asp Gln Pro Ala Asp Arg Asn
 80                  85                  90                  95

GCA GTG CCA AGA GAC GAT AAC CCA GGT AGA GCG AGA AGA AAG CGC ATG      144
Ala Val Pro Arg Asp Asp Asn Pro Gly Arg Ala Arg Arg Lys Arg Met
                100                 105                 110

AAA GTT CTA AAT GAG TCT GAA TGT CCG TGG CAT CCG TGG TGT GGC          189
Lys Val Leu Asn Glu Ser Glu Cys Pro Trp His Pro Trp Cys Gly
            115                 120                 125

TGATCGGAAT CCACGATTGC TATGACAGCC                                     219


(2) INFORMATION FOR SEQ ID NO:20:

     (i) SEQUENCE CHARACTERISTICS:
          (A) LENGTH: 63 amino acids
          (B) TYPE: amino acid
          (D) TOPOLOGY: linear

    (ii) MOLECULE TYPE: protein

    (xi) SEQUENCE DESCRIPTION: SEQ ID NO:20:

Met Gly Lys Leu Thr Ile Leu Val Leu Val Ala Ala Val Leu Leu Ser
  1             5                  10                  15

Thr Gln Val Met Val Gln Gly Asp Arg Asp Gln Pro Ala Asp Arg Asn
             20                  25                  30

Ala Val Pro Arg Asp Asp Asn Pro Gly Arg Ala Arg Arg Lys Arg Met
        35                  40                  45

Lys Val Leu Asn Glu Ser Glu Cys Pro Trp His Pro Trp Cys Gly
     50                  55                  60


(2) INFORMATION FOR SEQ ID NO:21:
```

-continued (i) SEQUENCE CHARACTERISTICS:
(A) LENGTH: 374 base pairs
(B) TYPE: nucleic acid
(C) STRANDEDNESS: double
(D) TOPOLOGY: linear (ii) MOLECULE TYPE: cDNA (vi) ORIGINAL SOURCE:
(A) ORGANISM: Conus radiatus (ix) FEATURE:
(A) NAME/KEY: CDS
(B) LOCATION: 94..282

(xi) SEQUENCE DESCRIPTION: SEQ ID NO:21:

```
CCGTCATCTA CACTCTCTGT CTCCCTGATT GCCGCCTTCA GTCGACCCGC CCTCATCCAG     60

CGCAGACTTG GTAAGAAGTG AAGAACCTTT ATC ATG GGG AAA CTG ACA ATA CTG     114
                                     Met Gly Lys Leu Thr Ile Leu
                                          65                  70

GTT CTT GTT GCT GCT GTC CTG TTG TCG GCC CAG GTC ATG GTT CAA GGT     162
Val Leu Val Ala Ala Val Leu Leu Ser Ala Gln Val Met Val Gln Gly
                75                  80                  85

GAC GGA GAT CAA CCT GCA GAT CGT AAT GCA GTG CCA AGA GAC GAT AAC     210
Asp Gly Asp Gln Pro Ala Asp Arg Asn Ala Val Pro Arg Asp Asp Asn
            90                  95                 100

CCA GGT GGA GCG AGT GGA AAG TTC ATG AAT GTT CTA CGT CGG TCT GGA     258
Pro Gly Gly Ala Ser Gly Lys Phe Met Asn Val Leu Arg Arg Ser Gly
        105                 110                 115

TGT CCG TGG GAA CCT TGG TGT GGC TGAACGGAAT CCACGATTGC AATGACAGCC     312
Cys Pro Trp Glu Pro Trp Cys Gly
    120                 125

GACAGAGCCG CACTCGAATT ATCTACAGTG GTGATGTCAG AGCATGATGT TTGAAAACGA    372

TC                                                                   374
```

(2) INFORMATION FOR SEQ ID NO:22:

(i) SEQUENCE CHARACTERISTICS:
(A) LENGTH: 63 amino acids
(B) TYPE: amino acid
(D) TOPOLOGY: linear (ii) MOLECULE TYPE: protein (xi) SEQUENCE DESCRIPTION: SEQ ID NO:22:

```
Met Gly Lys Leu Thr Ile Leu Val Leu Val Ala Ala Val Leu Leu Ser
  1               5                  10                  15

Ala Gln Val Met Val Gln Gly Asp Gly Asp Gln Pro Ala Asp Arg Asn
             20                  25                  30

Ala Val Pro Arg Asp Asp Asn Pro Gly Gly Ala Ser Gly Lys Phe Met
         35                  40                  45

Asn Val Leu Arg Arg Ser Gly Cys Pro Trp Glu Pro Trp Cys Gly
     50                  55                  60
```

(2) INFORMATION FOR SEQ ID NO:23:

(i) SEQUENCE CHARACTERISTICS:
(A) LENGTH: 8 amino acids
(B) TYPE: amino acid
(C) STRANDEDNESS:
(D) TOPOLOGY: linear (ii) MOLECULE TYPE: peptide (vi) ORIGINAL SOURCE:

-continued (A) ORGANISM: Conus radiatus (ix) FEATURE:
(A) NAME/KEY: Peptide
(B) LOCATION: 3..4
(D) OTHER INFORMATION: /note= "Xaa at residue 3 is Pro or 4-trans-hydroxyproline; Xaa at residue 4 is D-Trp or L-Trp."

(xi) SEQUENCE DESCRIPTION: SEQ ID NO:23:

Gly Cys Xaa Xaa Glu Pro Trp Cys
1 5

(2) INFORMATION FOR SEQ ID NO:24:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "primer"

(xi) SEQUENCE DESCRIPTION: SEQ ID NO:24:

ATGGGGAAAC TGACAATACT GG 22

(2) INFORMATION FOR SEQ ID NO:25:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "primer"

(xi) SEQUENCE DESCRIPTION: SEQ ID NO:25:

GGCTGTCATW CGAATCGTGG A 21

(2) INFORMATION FOR SEQ ID NO:26:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "primer"

(xi) SEQUENCE DESCRIPTION: SEQ ID NO:26:

GGCTTTTTTT TTTTTTTTTT TTTTTTTTTT TTT 33

(2) INFORMATION FOR SEQ ID NO:27:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "sequencing primer"

(xi) SEQUENCE DESCRIPTION: SEQ ID NO:27:

CACACAGGAA ACAGCTATG 19

-continued

```
(2) INFORMATION FOR SEQ ID NO:28:

     (i) SEQUENCE CHARACTERISTICS:
          (A) LENGTH: 17 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION: /desc = "oligomer for colony
               hybridization"

    (xi) SEQUENCE DESCRIPTION: SEQ ID NO:28:

CCRCACCANG GYTCCCA                                                    17


(2) INFORMATION FOR SEQ ID NO:29:

     (i) SEQUENCE CHARACTERISTICS:
          (A) LENGTH: 21 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION: /desc = "sequencing oligomer"

    (xi) SEQUENCE DESCRIPTION: SEQ ID NO:29:

TTGCATGCCT GCAGGTCGAC T                                               21
```